(12) United States Patent
DeRosa et al.

(10) Patent No.: US 10,864,267 B2
(45) Date of Patent: Dec. 15, 2020

(54) MESSENGER RNA THERAPY FOR TREATMENT OF ARTICULAR DISEASE

(71) Applicant: TRANSLATE BIO, INC., Cambridge, MA (US)

(72) Inventors: Frank DeRosa, Cambridge, MA (US); Michael Heartlein, Cambridge, MA (US)

(73) Assignee: TRANSLATE BIO, INC., Lexington, MA (US)

( * ) Notice: Subject to any disclaimer, the term of this patent is extended or adjusted under 35 U.S.C. 154(b) by 0 days.

(21) Appl. No.: 15/913,783

(22) Filed: Mar. 6, 2018

(65) Prior Publication Data

US 2018/0360961 A1    Dec. 20, 2018

Related U.S. Application Data

(63) Continuation of application No. 14/959,453, filed on Dec. 4, 2015, now Pat. No. 9,943,595.

(60) Provisional application No. 62/088,141, filed on Dec. 5, 2014.

(51) Int. Cl.
| | |
|---|---|
| A61K 9/127 | (2006.01) |
| A61K 31/7105 | (2006.01) |
| A61K 31/115 | (2006.01) |
| A61K 39/395 | (2006.01) |
| A61K 38/17 | (2006.01) |
| C07K 16/00 | (2006.01) |
| A61K 48/00 | (2006.01) |

(52) U.S. Cl.
CPC ........ *A61K 39/3955* (2013.01); *A61K 9/1272* (2013.01); *A61K 38/177* (2013.01); *A61K 48/005* (2013.01); *A61K 48/0025* (2013.01); *A61K 48/0075* (2013.01); *C07K 16/00* (2013.01); *A61K 48/00* (2013.01)

(58) Field of Classification Search
None
See application file for complete search history.

(56) References Cited

U.S. PATENT DOCUMENTS

| | | | |
|---|---|---|---|
| 5,705,385 A | | 1/1998 | Bally et al. |
| 5,858,355 A | † | 1/1999 | Glorioso |
| 5,976,567 A | | 11/1999 | Wheeler et al. |
| 5,981,501 A | | 11/1999 | Wheeler et al. |
| 6,004,942 A | † | 12/1999 | Firestein |
| 6,534,484 B1 | | 3/2003 | Wheeler et al. |
| 6,815,432 B2 | | 11/2004 | Wheeler et al. |
| 7,422,902 B1 | | 9/2008 | Wheeler et al. |
| 7,745,651 B2 | | 6/2010 | Heyes et al. |
| 7,799,565 B2 | | 9/2010 | MacLachlan et al. |
| 7,803,397 B2 | | 9/2010 | Heyes et al. |
| 7,901,708 B2 | | 3/2011 | MacLachlan et al. |
| 8,101,741 B2 | | 1/2012 | MacLachlan et al. |
| 8,188,263 B2 | | 5/2012 | MacLachlan et al. |
| 8,236,943 B2 | | 8/2012 | Lee et al. |
| 8,329,070 B2 | | 12/2012 | MacLachlan et al. |
| 8,513,403 B2 | | 8/2013 | MacLachlan et al. |
| 8,569,256 B2 | | 10/2013 | Heyes et al. |
| 8,710,200 B2 | | 4/2014 | Schrum et al. |
| 8,822,663 B2 | | 8/2014 | Chen et al. |
| 8,853,377 B2 | | 10/2014 | Guild et al. |
| 8,883,202 B2 | | 11/2014 | Manoharan et al. |
| 8,936,942 B2 | | 1/2015 | Heyes et al. |
| 8,980,864 B2 | | 3/2015 | Hoge et al. |
| 8,999,351 B2 | | 4/2015 | Manoharan et al. |
| 8,999,380 B2 | | 4/2015 | Bancel et al. |
| 8,999,950 B2 | | 4/2015 | MacLachlan et al. |
| 9,018,187 B2 | | 4/2015 | Heyes et al. |
| 9,051,567 B2 | | 6/2015 | Fitzgerald et al. |
| 9,061,059 B2 | | 6/2015 | Chakraborty et al. |
| 9,074,208 B2 | | 7/2015 | MacLachlan et al. |
| 9,089,604 B2 | | 7/2015 | Chakraborty et al. |
| 9,095,552 B2 | | 8/2015 | Chakraborty et al. |
| 9,107,886 B2 | | 8/2015 | Chakraborty et al. |
| 9,114,113 B2 | | 8/2015 | Chakraborty et al. |
| 9,181,319 B2 | | 11/2015 | Schrum et al. |
| 9,186,325 B2 | | 11/2015 | Manoharan et al. |
| 9,186,372 B2 | | 11/2015 | de Fougerolles et al. |
| 9,187,748 B2 | | 11/2015 | Geisbert et al. |
| 9,192,651 B2 | | 11/2015 | Chakraborty et al. |
| 9,220,755 B2 | | 12/2015 | Chakraborty et al. |

(Continued)

FOREIGN PATENT DOCUMENTS

| | | |
|---|---|---|
| CA | 2 807 552 A1 | 9/2012 |
| EP | 1 519 714 B1 | 10/2010 |

(Continued)

OTHER PUBLICATIONS

Mobasheri (Oct. 13, 2013) "The Future of Osteoarthritis Therapeutics: Emerging Biological Therapy", Current Rheumatology Reports, 15(12): article 385, 9 pages. (Year: 2013).*

Adriaansen, J., et al., Intraarticular Interferon-β Gene Therapy Ameliorates Adjuvant Arthritis in Rats, Human Gene Therapy, vol. 17, No. 10, Oct. 1, 2006, pp. 985-996.

Chen et al., "Suppression of collagen-induced arthritis by intraarticular lentiviral vector-mediated delivery of Toll-like receptor 7 short hairpin RNA gene", Gene Therapy, 19: 752-760 (2012).

Flory, C., et al., Nuclease-resistant ribozymes decrease stromelysin mRNA levels in rabbit synvium following exogenous delivery to the knee joint, Proceedings of the National Academy of Sciences, vol. 93, pp. 754-758, Jan. 23, 1996.

(Continued)

*Primary Examiner* — Robert M Kelly
(74) *Attorney, Agent, or Firm* — Proskauer Rose LLP; Fangli Chen

(57) ABSTRACT

The present invention provides, among other things, a method of intra-articular delivery of messenger RNA (mRNA), comprising administering into a joint of a subject in need of delivery a composition comprising an mRNA encoding a protein, such that the administering of the composition results in expression of the protein encoded by the mRNA in the joint.

15 Claims, 4 Drawing Sheets

Specification includes a Sequence Listing.

(56) References Cited

U.S. PATENT DOCUMENTS

| | | |
|---|---|---|
| 9,220,792 B2 | 12/2015 | Chakraborty et al. |
| 9,233,141 B2 | 1/2016 | Chakraborty et al. |
| 9,254,311 B2 | 2/2016 | Bancel et al. |
| 9,295,689 B2 | 3/2016 | de Fougerolles et al. |
| 9,301,993 B2 | 4/2016 | Chakraborty et al. |
| 9,303,079 B2 | 4/2016 | Chakraborty et al. |
| 9,334,328 B2 | 5/2016 | Schrum et al. |
| 9,345,780 B2 | 5/2016 | Manoharan et al. |
| 9,352,042 B2 | 5/2016 | Heyes et al. |
| 9,352,048 B2 | 5/2016 | Manoharan et al. |
| 9,364,435 B2 | 6/2016 | Yaworski et al. |
| 9,370,581 B2 | 6/2016 | Manoharan et al. |
| 9,370,582 B2 | 6/2016 | Manoharan et al. |
| 10,087,247 B2 * | 10/2018 | Heartlein ............... C07K 16/22 |
| 10,143,758 B2 * | 12/2018 | Guild ................... A61K 9/0019 |
| 2002/0192651 A1 | 12/2002 | Wheeler et al. |
| 2003/0181410 A1 | 9/2003 | Wheeler et al. |
| 2004/0142025 A1 | 7/2004 | MacLachlan et al. |
| 2006/0008910 A1 | 1/2006 | MacLachlan et al. |
| 2006/0083780 A1 | 4/2006 | Heyes et al. |
| 2007/0135372 A1 | 6/2007 | MacLachlan et al. |
| 2007/0212362 A1 † | 9/2007 | Filvaroff |
| 2009/0270481 A1 | 10/2009 | MacLachlan et al. |
| 2010/0041152 A1 | 2/2010 | Wheeler et al. |
| 2011/0244026 A1 | 10/2011 | Guild et al. |
| 2011/0256175 A1 | 10/2011 | Hope et al. |
| 2011/0311583 A1 | 12/2011 | Manoharan et al. |
| 2012/0065252 A1 | 3/2012 | Schrum et al. |
| 2012/0128760 A1 | 5/2012 | Manoharan et al. |
| 2012/0142756 A1 | 6/2012 | Guild et al. |
| 2012/0202871 A1 | 8/2012 | Heyes et al. |
| 2012/0237975 A1 | 9/2012 | Schrum et al. |
| 2012/0251618 A1 | 10/2012 | Schrum et al. |
| 2012/0328668 A1 | 12/2012 | MacLachlan et al. |
| 2013/0195967 A1 | 8/2013 | Guild et al. |
| 2013/0237594 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2014/0010861 A1 | 1/2014 | Bancel et al. |
| 2014/0044772 A1 | 2/2014 | MacLachlan et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0171485 A1 | 6/2014 | Bancel et al. |
| 2014/0179756 A1 | 6/2014 | MacLachlan et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221465 A1 | 8/2014 | Bancel et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0294937 A1 | 10/2014 | MacLachlan et al. |
| 2014/0343129 A1 | 11/2014 | de Fougerolles et al. |
| 2015/0005372 A1 | 1/2015 | Hoge et al. |
| 2015/0017211 A1 | 1/2015 | de Fougerolles et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0111945 A1 | 4/2015 | Geisbert et al. |
| 2015/0166465 A1 | 6/2015 | Chen et al. |
| 2015/0190515 A1 | 7/2015 | Manoharan et al. |
| 2015/0265708 A1 | 9/2015 | Manoharan et al. |
| 2015/0315541 A1 | 11/2015 | Bancel et al. |
| 2015/0315584 A1 | 11/2015 | MacDonald et al. |
| 2015/0366997 A1 | 12/2015 | Guild et al. |
| 2016/0095924 A1 | 4/2016 | Hope et al. |
| 2016/0114011 A1 | 4/2016 | Bancel et al. |
| 2016/0115477 A1 | 4/2016 | MacLachlan et al. |
| 2016/0115483 A1 | 4/2016 | MacLachlan et al. |
| 2016/0136236 A1 | 5/2016 | Hoge et al. |
| 2016/0151284 A1 | 6/2016 | Heyes et al. |
| 2016/0158385 A1 | 6/2016 | Bancel et al. |

FOREIGN PATENT DOCUMENTS

| | | |
|---|---|---|
| EP | 2 449 106 | 5/2012 |
| EP | 2 338 478 A1 | 6/2013 |
| EP | 2 823 809 A1 | 1/2015 |
| WO | WO2004/011647 A1 | 2/2004 |
| WO | WO2005/026372 A1 | 3/2005 |
| WO | WO2005/115481 A1 | 12/2005 |
| WO | WO2005/121348 A1 | 12/2005 |
| WO | WO2009/127060 A1 | 10/2006 |
| WO | 2009003211 A1 † | 1/2009 |
| WO | WO2009/003211 A1 | 1/2009 |
| WO | WO 2009/058881 | 5/2009 |
| WO | WO2009/073930 A1 | 6/2009 |
| WO | WO2010/042877 A1 | 4/2010 |
| WO | WO2011/141705 A1 | 11/2011 |
| WO | WO2012/019168 A1 | 2/2012 |
| WO | WO2012/135805 A2 | 10/2012 |
| WO | WO2012/170930 A1 | 12/2012 |
| WO | WO2013/039857 A1 | 3/2013 |
| WO | WO2013/039861 A2 | 3/2013 |
| WO | WO2013/090186 A1 | 6/2013 |
| WO | WO2013/101690 A1 | 7/2013 |
| WO | WO2013/126803 A1 | 8/2013 |
| WO | WO2013/130161 A1 | 9/2013 |
| WO | WO 2013/149140 | 10/2013 |
| WO | WO2013/151663 A1 | 10/2013 |
| WO | WO2013/151664 A1 | 10/2013 |
| WO | WO2013/151666 A2 | 10/2013 |
| WO | WO2013/151667 A1 | 10/2013 |
| WO | WO2013/151668 A2 | 10/2013 |
| WO | WO2013/151670 A2 | 10/2013 |
| WO | WO2013/151671 A1 | 10/2013 |
| WO | WO2013/151672 A2 | 10/2013 |
| WO | WO2013/151736 A2 | 10/2013 |
| WO | 2013185069 A1 † | 12/2013 |
| WO | WO 2013/182683 | 12/2013 |
| WO | WO2013/185069 A1 | 12/2013 |
| WO | WO2014/089486 A1 | 6/2014 |
| WO | WO2014/113089 A2 | 7/2014 |
| WO | 2014152211 A1 † | 9/2014 |
| WO | WO2014/144039 A1 | 9/2014 |
| WO | WO2014/144711 A1 | 9/2014 |
| WO | WO2014/144767 A1 | 9/2014 |
| WO | WO2014/152027 A1 | 9/2014 |
| WO | WO2014/152030 A1 | 9/2014 |
| WO | WO2014/152031 A1 | 9/2014 |
| WO | WO2014/152211 A1 | 9/2014 |
| WO | WO2014/152540 A1 | 9/2014 |
| WO | WO 2014/152774 | 9/2014 |
| WO | WO2014/158795 A1 | 10/2014 |
| WO | WO2014/159813 A1 | 10/2014 |
| WO | WO2015/006747 A2 | 1/2015 |

(56) References Cited

FOREIGN PATENT DOCUMENTS

| | | |
|---|---|---|
| WO | WO2015/024668 A2 | 2/2015 |
| WO | WO2015/011633 A1 | 4/2015 |
| WO | WO2015/048744 A2 | 4/2015 |
| WO | WO2015/051169 A2 | 4/2015 |
| WO | WO2015/051173 A2 | 4/2015 |
| WO | WO2015/058069 A1 | 4/2016 |
| WO | WO2016/054421 A1 | 4/2016 |
| WO | WO2016/071857 A1 | 5/2016 |
| WO | WO2016/077123 A1 | 5/2016 |
| WO | WO2016/077125 A1 | 5/2016 |
| WO | WO2016/100812 A1 | 6/2016 |

OTHER PUBLICATIONS

Gilboa, E., mRNA Leapfrogs DNA to Show Promise for Therapeutic Gene Transfer, Molecular Therapy, vol. 20, No. 4 Apr. 2012.

Heyes et al., "Cationic lipid saturation influences intracellular delivery of encapsulated nucleic acids", Journal of Controlled Release, 107(2): 276-87 (2005).

Kariko et al., "Increased Erythropoiesis in Mice Injected With Submicrogram Quantities of Pseudouridine-containing mRNA Encoding Erythropoietin", Molecular Therapy, 20(5): 948-53. (2012).

Keffer et al., "Transgenic mice expressing human tumor necrosis factor: a predictive genetic model of arthritis", EMBO Journal, 10(13): 4025-31 (1991).

Pinto, L., et al., IL-17 mediates articular hypernociception in antigen-induced arthritis in mice, Pain, Elsevier Science Publishers, Amstrerdam, NL, vol. 148, No. 2, Feb. 1, 2010, pp. 247-256.

Song et al. "Characterization of a novel anti-human TNF-a murine monoclonal antibody with high binding affinity and neutralizing activity", Experimental and Molecular Medicine, 40(1): 35-42 (2008).

Su et al., "In vitro and in vivo mRNA delivery using lipid-enveloped pH-responsive polymer nanoparticles", Molecular Pharmacology, 8(3): 774-87 (2011).

Tavernier et al. "mRNA as a gene therapeutic: How to control protein expression", Journal of Controlled Release, 150(3): 238-47 (2011).

Traister and Hirsch, "Gene therapy for arthritis"., Mod Rheumatol., 18: 2-14 (2008).

Yorimitsu, M. et al., Intra-articular injection of interleukin-4 decreases nitric oxide production by chondrocytes and ameliorates subsequent destruction of cartilage in instability-induced osteoarthritis in rat knee joints, Osteoarthritis and Cartilage, Bailliere Tindall, London, GB, vol. 16, No. 7, Jul. 1, 2008, pp. 764-771.

Zhang et al., "Direct chitosan-mediated gene delivery to the rabbit knee joints in vitro and in vivo", Biochemical and Biophysical Research Communications, 341: 202-208 (2006).

European Journal of Pharmaceutics and Biopharmaceutics, 2009, 71, p. 484-489.

Chen et al., "Suppression of collagen-induced arthritis by intra-articular lentiviral vector-mediated delivery of Toll-like receptor 7 short hairpin RNA gene," Gene There., 19:752-60, 2012.†

Madry et al., "Gene therapy for cartilage repair," Cartilage, 2(3):201-225, 2011.†

Traister et al., "Gene therapy for arthritis," Mod. Rhematol., 18:2-14, 2008.†

\* cited by examiner
† cited by third party

Figure 1A    Figure 1B
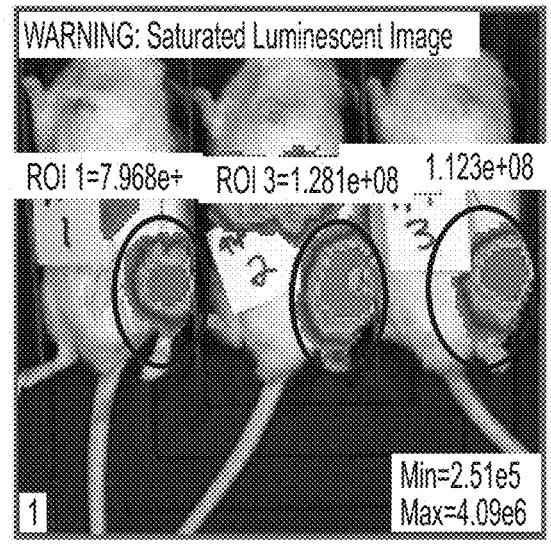
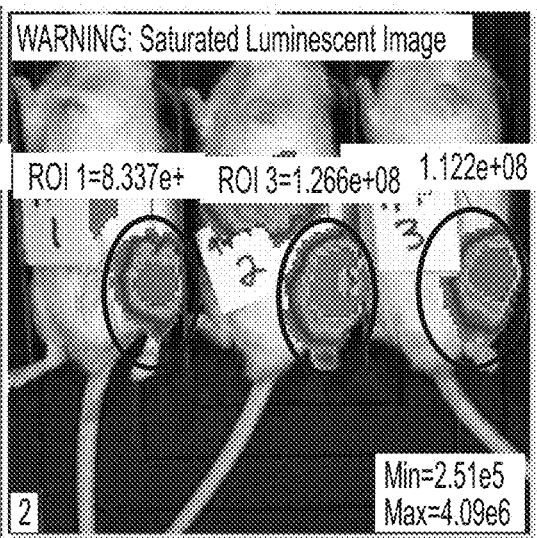
Figure 1C
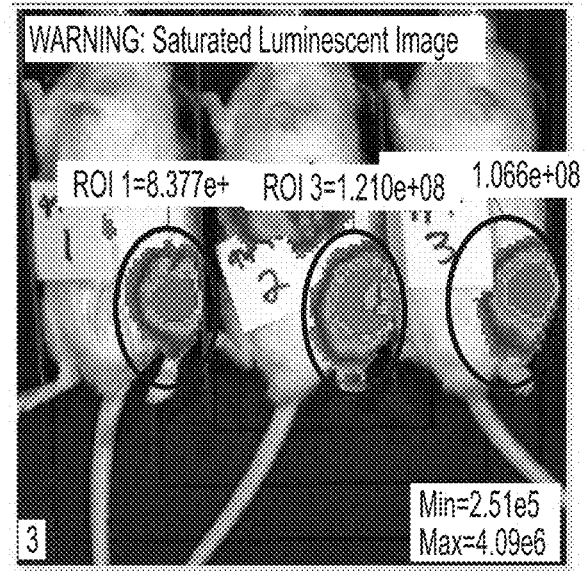
Figures 1A-1C

Figure 2A
Figure 2B
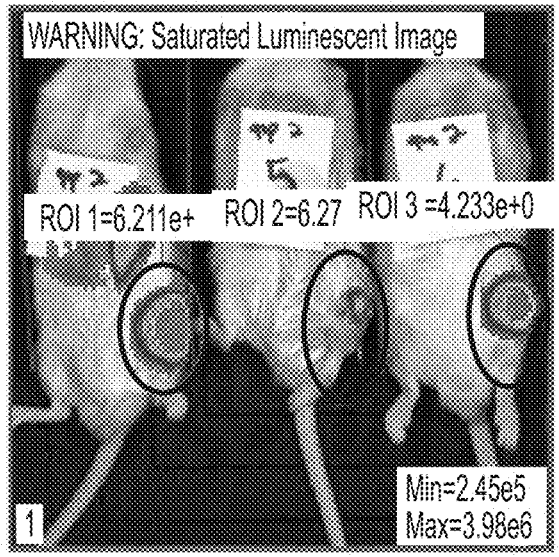
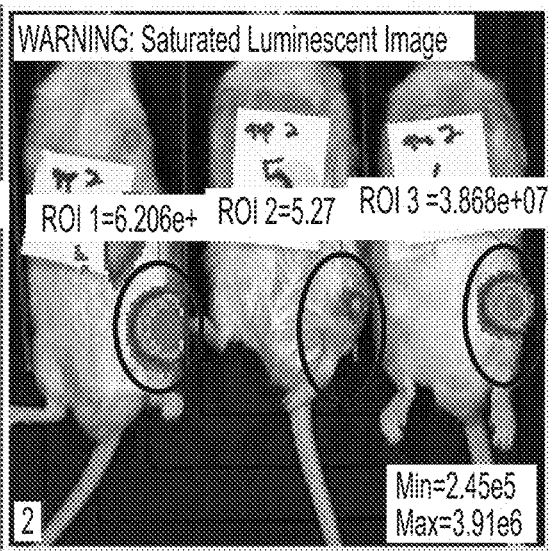
Figure 2C
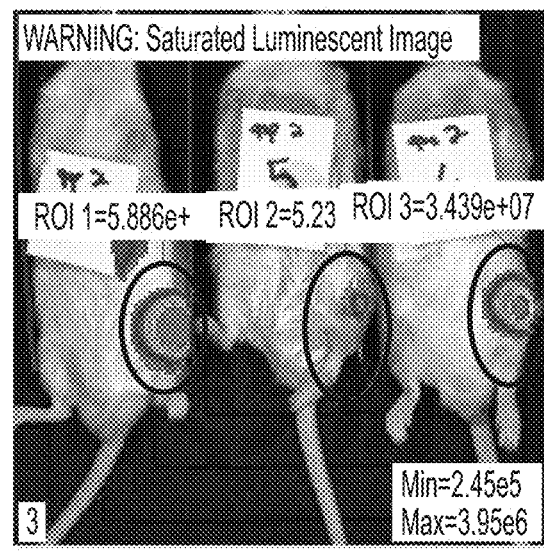
Figures 2A-2C

Figure 3A
Figure 3B
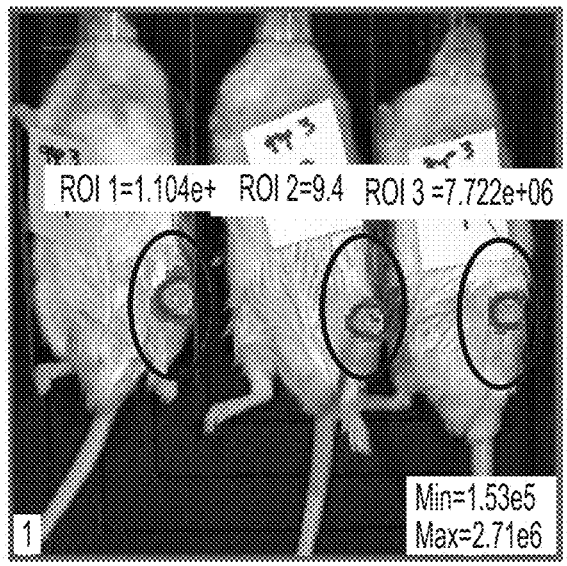
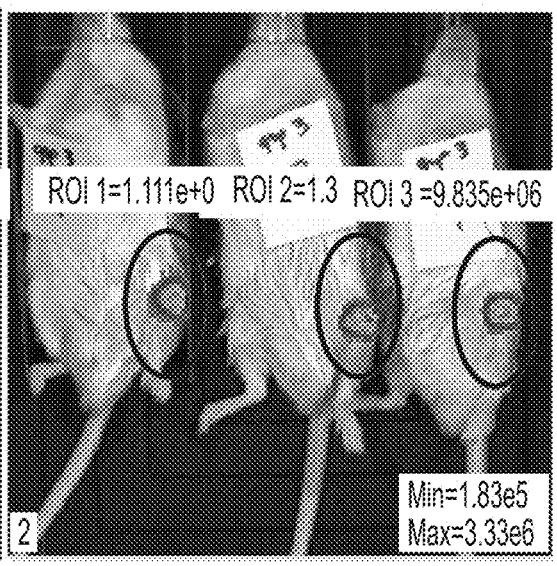
Figure 3C
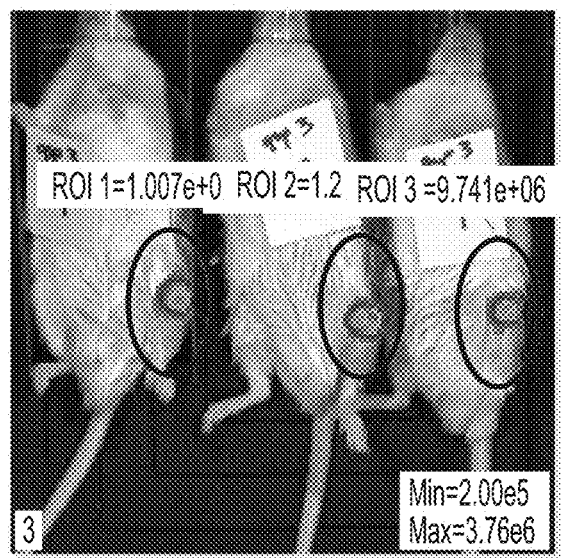
Figures 3A-3C

Figure 4A 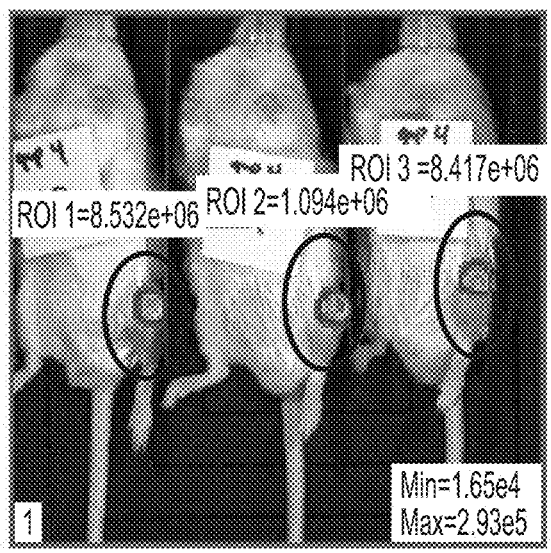 Figure 4B 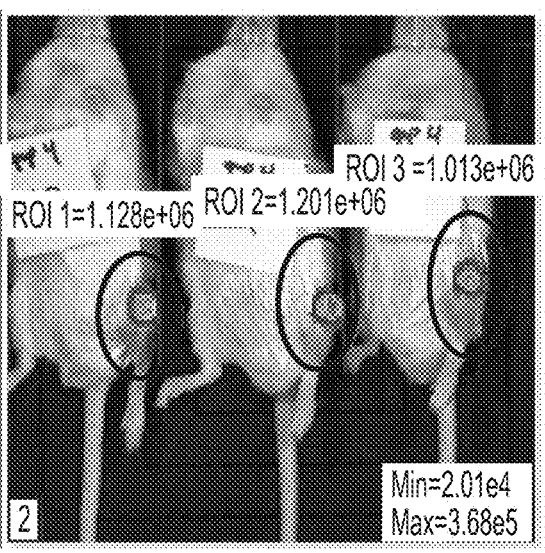
Figure 4C
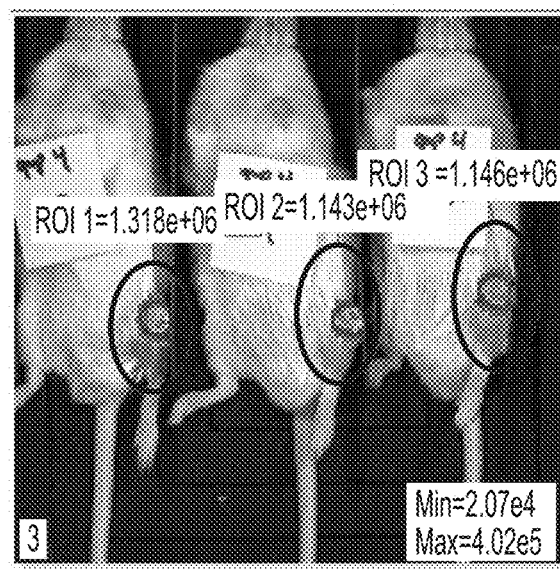
Figures 4A-4C

SEQUENCE LISTING

```
<160> NUMBER OF SEQ ID NOS: 4

<210> SEQ ID NO 1
<211> LENGTH: 1898
<212> TYPE: RNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1794)..(1794)
<223> OTHER INFORMATION: May or maynot be present
<220> FEATURE:
<221> NAME/KEY: modified_base
<222> LOCATION: (1896)..(1896)
<223> OTHER INFORMATION: May or maynot be present

<400> SEQUENCE: 1
ggacagaucg ccuggagacg ccauccacgc uguuuugacc uccauagaag acaccgggac      60
cgauccagcc uccgcggccg ggaacggugc auuggaacgc ggauucuccg ugccaagagu     120
gacucaccgu ccuugacacg auggaagaug ccaaaaacau uaagaagggc ccagcgccau     180
ucuacccacu cgaagacggg accgccggcg agcagcugca caaagccaug aagcgcuacg     240
cccuggugcc cggcaccauc gccuuuaccg acgcacauau cgagguggac auuaccuacg     300
ccgaguacuu cgagaugagc guucggcugg cagaagcuau gaagcgcuau gggcugaaua     360
caaaccaucg gaucguggug ugcagcgaga auagcuugca guucuucaug cccguguugg     420
gugcccuguu caucggugug gcuguggccc cagcuaacga caucuacaac gagcgcgagc     480
ugcugaacag caugggcauc agccagccca ccgucguauu cgugagcaag aaagggcugc     540
aaaagauccu caacgugcaa aagaagcuac cgaucauaca aaagaucauc aucauggaua     600
gcaagaccga cuaccagggc uuccaaagca uguacacuu cgugacuucc cauuugccac     660
ccggcuucaa cgaguacgac uucgugcccg agagcuucga ccgggacaaa accaucgccc     720
ugaucaugaa caguaguggc aguaccggau ugccaaggg cguagcccua ccgcaccgca     780
ccgcuugugu ccgauucagu caugcccgcg accccaucuu cggcaaccag aucauccccg     840
acaccgcuau cccucagcgug gugccauuuc accacgccuu cggcauguuc accacgcugg     900
gcuacuugau cugcggcuuu cgggucgugc ucauguaccg cuucgaggag gagcuauucu     960
ugcgcagcuu gcaagacuau aagauucaau cugcccugcu ggugcccaca cuauuuagcu    1020
```

```
ucuucgcuaa gagcacucuc aucgacaagu acgaccuaag caacuugcac gagaucgcca    1080
gcggcggggc gccgcucagc aaggagguag gugaggccgu ggccaaacgc uuccaccuac    1140
caggcauccg ccagggcuac ggccugacag aaacaaccag cgccauucug aucaccccg     1200 aaggggacga caagccuggc gcaguaggca aggugguggcc cuucuucgag gcuaaggugg   1260
uggacuugga caccgguaag acacggggug ugaaccagcg cggcgagcug ugcguccgug   1320
gccccaugau caugagcggc uacguuaaca accccgaggc uacaaacgcu cucaucgaca    1380
aggacggcug gcugcacagc ggcgacaucg ccuacuggga cgaggacgag cacuucuuca    1440
ucguggaccg gcugaagagc cugaucaaau acaagggcua ccagguagcc ccagccgaac   1500
uggagagcau ccugcugcaa caccccaaca ucuucgacgc cggggucgcc ggccugcccg    1560
acgacgaugc cggcgagcug cccgccgcag ucgucgugcu ggaacacggu aaaaccauga   1620
ccgagaagga gaucguggac uauguggcca gccagguuac aaccgccaag aagcugcgcg   1680
gugguguugu guucguggac gaggugccua aaggacugac cggcaaguug gacgcccgca   1740
agauccgcga gauucucauu aaggccaaga agggcggcaa gaucgccgug uaacggguggg   1800 caucccugug accccucccc agugccucuc cuggcccugg aaguugccac uccagugccc    1860
accagccuug uccuaauaaa auuaaguugc aucaagcu                            1898

<210> SEQ ID NO 2
<211> LENGTH: 140
<212> TYPE: RNA
<213> ORGANISM: Artificial Sequence
<220> FEATURE:
<223> OTHER INFORMATION: Synthetic Polynucleotide

<400> SEQUENCE: 2
ggacagaucg ccuggagacg ccauccacgc uguuuugacc uccauagaag acaccgggac     60
cgauccagcc uccgcggccg ggaacggugc auuggaacgc ggauucccccg ugccaagagu   120 gacucaccgu ccuugacacg                                                140

<210> SEQ ID NO 3
<211> LENGTH: 105
<212> TYPE: RNA
<213> ORGANISM: Artificial Sequence
<220> FEATURE:
<223> OTHER INFORMATION: Synthetic Polynucleotide

<400> SEQUENCE: 3
cggguggcau cccugugacc ccuccccagu gccucuccug gcccuggaag uugccacucc     60
agugcccacc agccuugucc uaauaaaauu aaguugcauc aagcu                    105

<210> SEQ ID NO 4
<211> LENGTH: 105
<212> TYPE: RNA
<213> ORGANISM: Artificial Sequence
<220> FEATURE:
<223> OTHER INFORMATION: Synthetic Polynucleotide

<400> SEQUENCE: 4
ggguggcauc ccugugaccc cuccccagug ccucuccugg cccuggaagu ugccacucca     60
gugcccacca gccuuguccu aauaaaauua aguugcauca aagcu                    105
```

MESSENGER RNA THERAPY FOR TREATMENT OF ARTICULAR DISEASE

RELATED APPLICATIONS

This application is a continuation application of U.S. patent application Ser. No. 14/959,453, filed on Dec. 4, 2015, issued as U.S. Pat. No. 9,943,595 on Apr. 17, 2018, which claims priority to U.S. Provisional Application Ser. No. 62/088,141, filed Dec. 5, 2014, the disclosures of which are hereby incorporated in their entirety.

SEQUENCE LISTING

The present specification makes reference to a Sequence listing (submitted as a .txt. file named MRT1177US2_SequenceListing_ST25.txt), generated on Aug. 1, 2018 as a substitute computer readable form in response to the Notice to File Missing Parts issued by the USPTO on Apr. 11, 2018. The .txt file is 3,982 bytes in size. The entire contents of the Sequence is incorporated herein by reference.

BACKGROUND

Effective therapies are still needed for the treatment of articular diseases, disorders or conditions such as those directly or indirectly resulting from the loss, aberrant expression, dysregulation or over-production of a protein associated with or located in a joint. Several hurdles exist in implementing an effective treatment strategy for articular diseases and disorders, mainly due to the unique anatomy and physiology of joints.

SUMMARY OF THE INVENTION

The present invention provides, among other things, effective methods and compositions for the treatment of articular diseases, disorders or conditions based on messenger RNA (mRNA) therapy. The present invention is, in part, based on unexpected observation that mRNA may be effectively delivered to joints despite the complex and unique anatomy and physiology of joints. As described herein, including in the examples, the present inventors have successfully delivered mRNA, resulting in robust protein expression throughout the knee joint. Therefore, the present inventors have demonstrated, for the first time, that mRNA based delivery may be used to effectively deliver therapeutic proteins in a joint for treatment of articular diseases, disorders or conditions.

Thus, in one aspect, the present invention provides a method of intra-articular delivery of messenger RNA (mRNA), comprising administering into a joint of a subject in need of delivery a composition comprising one or more mRNAs encoding one or more polypeptides, such that the administering of the composition results in expression of the one or more polypeptides encoded by the one or more mRNAs in the joint.

In some embodiments, the composition is administered locally into a joint. In some embodiments, the joint is a fibrous joint, a cartilaginous joint, or a synovial joint. In certain embodiments, the joint is a synovial joint. In some embodiments, the composition is administered directly into the synovial cavity.

In some embodiments, the expression and/or activity of the one or more polypeptides is detected in cartilage, ligament, muscle, synovial intimal cells, chondrocytes and/or fluids of the joint.

In some embodiments, the expression and/or activity of the one or more polypeptides is detectable at least about 6 hours, 12 hours, 18 hours, 24 hours, 2 days, 3 days, 4 days, 5 days, 6 days, 1 week, 2 weeks, 3 weeks, 4 weeks, or 1 month post-administration.

In some embodiments, each of the one or more mRNAs has a length of or greater than about 0.5 kb, 1 kb, 1.5 kb, 2 kb, 2.5 kb, 3 kb, 3.5 kb, 4 kb, 4.5 kb, 5 kb, 6kb, 7 kb, 8 kb, 9 kb, 10 kb, 11 kb, 12 kb, 13 kb, 14 kb, or 15 kb.

In some embodiments, the one or more polypeptides encoded by the one or more mRNAs normally function in the joint.

In some embodiments, the one or more polypeptides encoded by the one or more mRNAs are anti-inflammatory.

In some embodiments, the one or more mRNAs encode an antibody. In some embodiments, the antibody is an intact immunoglobulin, $(Fab)_2$, $(Fab')_2$, Fab, Fab' or scFv. In some embodiments, the one or more mRNAs encode antibody heavy chain, light chain, or fragment thereof. In some embodiments, the composition comprises two distinct mRNAs encoding antibody heavy chain and light chain, respectively.

In some embodiments, the antibody encoded by the one or more mRNAs is an anti-TNFα antibody, anti-IL-6 antibody, anti-IL-1β antibody, anti-sTNFR-I antibody, anti-sTNFR-II antibody, anti-IL-2 antibody, anti-IFN-γ antibody, anti-IL-18 antibody, anti-IL-12 antibody, or anti-IL-12p40 antibody.

In some embodiments, the one or more mRNAs encode a soluble receptor.

In another aspect, the present invention provides a method of treating a joint disease, disorder or condition, comprising delivering one or more mRNAs using a method described herein.

In some embodiments, the joint disease, disorder or condition is an inflammatory disease, disorder or condition. In some embodiments, the inflammatory disease, disorder or condition is arthritis. In some embodiments, the inflammatory disease, disorder or condition is selected from the group consisting of rheumatoid arthritis, psoriatic arthritis, gout, pseudogout, tendinitis, bursitis, Carpal Tunnel Syndrome, osteoarthritis, synovitis, spondylitis, amyloidosis, lumbar spinal stenosis, and/or sacroiliac joint dysfunction.

In some embodiments, the composition is administered once a week. In some embodiments, the composition is administered twice a month. In some embodiments, the composition is administered once a month.

In some embodiments, the one or more mRNAs are encapsulated within one or more nanoparticles. In some embodiments, the one or more nanoparticles are lipid or polymer based nanoparticles. In some embodiments, the one or more nanoparticles comprise a liposome. In some embodiments, the liposome comprises one or more cationic lipids, one or more non-cationic lipids, one or more cholesterol-based lipids and one or more PEG-modified lipids.

In some embodiments, the one or more cationic lipids are selected from the group consisting of C12-200, MC3, DLinDMA, DLinkC2DMA, cKK-E12, ICE (Imidazol-based), HGT5000, HGT5001, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, HGT4003, and combinations thereof.

In some embodiments, the one or more cationic lipids comprise cKK-E12:

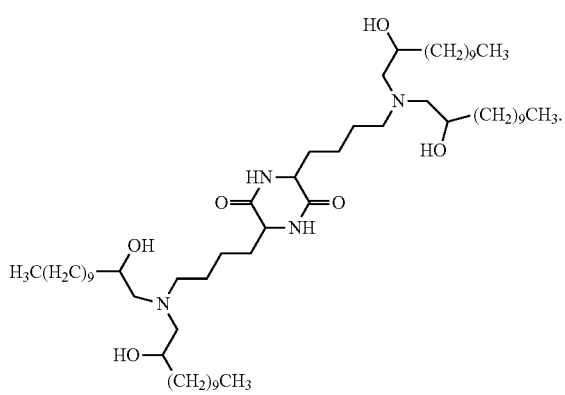

In some embodiments, the one or more non-cationic lipids are selected from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPA (1,2-dioleyl-sn-glycero-3-phosphotidykholine) DPPE (1,2-dipalmitoyl-su-glycero-3-phosphoethanolamine), DMPE (12-dimyristoyl-sn-glycero-3-phosphoethanolamine), DOPG (2-dioleoyl-sn-glycero-3-phospho-(1'-rac-glycerol)).

In some embodiments, the one or more cholesterol-based lipids is cholesterol or PEGylated cholesterol.

In some embodiments, the one or more PEG-modified lipids comprise a poly(ethylene) glycol chain of up to 5 kDa in length covalently attached to a lipid with alkyl chain(s) of $C_6$-$C_{20}$ length.

In some embodiments, the cationic lipid constitutes about 30-70% of the liposome by molar ratio.

In some embodiments, the liposome comprises cKK-E12, DOPE, cholesterol, and DMG-PEG2K. In some embodiments, the liposome comprises cKK-E12, DOPE, cholesterol, and DMG-PEG2K at a ratio of about 50:25:20:5, 50:20:25:5, 50:27:20:3, 40:30:20:10, 40:30:25:5, or 40:32:25:3.

In some embodiments, the liposome comprises C12-200, DOPE, cholesterol and DMG-PEG2K. In some embodiments, the liposome comprises C12-200, DOPE, cholesterol and DMG-PEG2K at a ratio of about 50:25:20:5, 50:20:25:5, 50:27:20:3, 40:30:20:10, 40:30:25:5, or 40:32:25:3.

In some embodiments, the liposome comprises HGT5001, DOPE, cholesterol and DMG-PEG2K. In some embodiments, the liposome comprises HGT5001, DOPE, cholesterol and DMG-PEG2K at a ratio of about 50:25:20:5, 50:20:25:5, 50:27:20:3, 40:30:20:10, 40:30:25:5, or 40:32:25:3.

In some embodiments, the nanoparticles comprise a polymer based nanoparticle. In some embodiments, the polymer based nanoparticle comprises PEI. In some embodiments, the PEI is branched PEI.

In some embodiments, the nanoparticles have a size less than about 40-100 nm. As used herein, the size of a nanoparticle is defined by the largest diameter of the particle.

In some embodiments, the one or more mRNAs comprise one or more modified nucleotides. In some embodiments, the one or more modified nucleotides comprise pseudouridine, N-1-methyl-pseudouridine, 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and/or 2-thiocytidine.

In some embodiments, the one or more mRNAs are unmodified.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWING

The drawings are for illustration purposes only not for limitation.

FIGS. 1A-1C depict exemplary visualization of firefly luciferase luminescence as measured via IVIS imaging. The protein detected is a result of its production from FFL mRNA delivered via intra-articular administration using cKK-E12-based lipid nanoparticles (5.0 micrograms, based on encapsulated mRNA).

FIGS. 2A-2C depict exemplary visualization of firefly luciferase luminescence in wild type mice as measured via IVIS imaging. The protein detected is a result of its production from FFL mRNA delivered via intra-articular administration using C12-200-based lipid nanoparticles (5.0 micrograms, based on encapsulated mRNA).

FIGS. 3A-3C depicts exemplary visualization of firefly luciferase luminescence in wild type mice as measured via IVIS imaging. The protein detected is a result of its production from FFL mRNA delivered via intra-articular administration using HGT5001-based lipid nanoparticles (2.5 micrograms, based on encapsulated mRNA).

FIGS. 4A-4C depicts exemplary visualization of firefly luciferase luminescence in wild type mice as measured via IVIS imaging. The protein detected is a result of its production from FFL mRNA delivered via intra-articular administration using 25 kDa branched PEI-based lipid nanoparticles (2.5 micrograms, based on encapsulated mRNA).

DEFINITIONS

In order for the present invention to be more readily understood, certain terms are first defined below. Additional definitions for the following terms and other terms are set forth throughout the specification.

Alkyl: As used herein, "alkyl" refers to a radical of a straight-chain or branched saturated hydrocarbon group having from 1 to 15 carbon atoms ("C1-15 alkyl"). In some embodiments, an alkyl group has 1 to 3 carbon atoms ("C1-3 alkyl"). Examples of C1-3 alkyl groups include methyl (C1), ethyl (C2), n-propyl (C3), and isopropyl (C3). In some embodiments, an alkyl group has 8 to 12 carbon atoms ("C8-12 alkyl"). Examples of C8-12 alkyl groups include, without limitation, n-octyl (C8), n-nonyl (C9), n-decyl (C10), n-undecyl (C11), n-dodecyl (C12) and the like. The prefix "n-" (normal) refers to unbranched alkyl groups. For example, n-C8 alkyl refers to —(CH2)7CH3, n-C10 alkyl refers to —(CH2)9CH3, etc.

Amelioration: As used herein, the term "amelioration" is meant the prevention, reduction or palliation of a state, or improvement of the state of a subject. Amelioration includes, but does not require complete recovery or complete prevention of a disease condition. In some embodiments, amelioration includes increasing levels of relevant protein or its activity that is deficient in relevant disease tissues.

Amino acid: As used herein, term "amino acid," in its broadest sense, refers to any compound and/or substance that can be incorporated into a polypeptide chain. In some embodiments, an amino acid has the general structure $H_2N$—C(H)(R)—COOH. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Articular disease, disorder or condition: As used herein, the term "articular disease, disorder or condition" refers to a disease, disorder or condition affecting a joint, a structure of a joint and/or articulated movement. Thus an articular disease, disorder or condition is also referred to as a joint disease, disorder or condition.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery").

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein. In this application, the terms "expression" and "production," and grammatical equivalent, are used inter-changeably.

Fragment: The term "fragment" as used herein refers to polypeptides and is defined as any discrete portion of a given polypeptide that is unique to or characteristic of that polypeptide. The term as used herein also refers to any discrete portion of a given polypeptide that retains at least a fraction of the activity of the full-length polypeptide. Preferably the fraction of activity retained is at least 10% of the activity of the full-length polypeptide. More preferably the fraction of activity retained is at least 20%, 30%, 40%, 50%, 60%, 70%, 80% or 90% of the activity of the full-length polypeptide. More preferably still the fraction of activity retained is at least 95%, 96%, 97%, 98% or 99% of the activity of the full-length polypeptide. Most preferably, the fraction of activity retained is 100% of the activity of the full-length polypeptide. The term as used herein also refers to any portion of a given polypeptide that includes at least an established sequence element found in the full-length polypeptide. Preferably, the sequence element spans at least 4-5, more preferably at least about 10, 15, 20, 25, 30, 35, 40, 45, 50 or more amino acids of the full-length polypeptide.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Joint: As used herein, the term "joint" refers to a structure or location at which bones connect. A joint is also referred to an articulation (or articulate surface).

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre and post natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, non-toxic ammonium. quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treatment: As used herein, the term "treatment" (also "treat" or "treating") refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition (e.g., influenza). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

DETAILED DESCRIPTION

The present invention provides, among other things, methods and compositions for treating joint diseases, disorders and conditions based on mRNA therapy. In particular, the present invention provides methods for treating joint diseases, disorders and conditions by administering to a subject in need of treatment a composition comprising one or more mRNAs encoding one or more polypeptides suitable for the treatment of the joint diseases, disorders and conditions (e.g., therapeutic polypeptides). In some embodiments, the one or more mRNAs are encapsulated within one or more lipid and/or polymer based nanoparticles. In some embodiments, the one or more mRNAs are encapsulated within one or more liposomes. As used herein, the term "liposome" refers to any lamellar, multilamellar, or solid nanoparticle vesicle. Typically, a liposome as used herein can be formed by mixing one or more lipids or by mixing one or more lipids and polymer(s). In some embodiments, a liposome suitable for the present invention contains cationic lipids(s), non-cationic lipid(s), cholesterol-based lipid(s) and PEG-modified lipid(s).

Various aspects of the invention are described in detail in the following sections. The use of sections is not meant to limit the invention. Each section can apply to any aspect of the invention. In this application, the use of "or" means "and/or" unless stated otherwise.

Articular Diseases, Disorders or Conditions

The present invention may be used to treat a subject who is suffering from or susceptible to an articular disease, disorder or condition. As used herein, an "articular disease, disorder or condition" refers to a disease, disorder or condition affecting a joint, a structure of a joint and/or articulated movement. Thus an articular disease, disorder or condition is also referred to as a joint disease, disorder or condition. Articular diseases, disorders or conditions can affect any type of joint or any structure of a joint. In some embodiments, the structure of a joint includes bones, ligaments, tendons, cartilage, muscle, bursa, and/or synovial membranes. Typically, articular diseases, disorders or conditions described herein may affect fibrous joints, cartilaginous joints, and/or synovial joints. In some embodiments, articular diseases, disorders or conditions described herein affect synovial joint.

In some embodiments, articular diseases, disorders or conditions described herein may affect joints classified as articulations of the hand, elbow joints, wrist joints, axillary articulations, sternoventricular joints, vertebral articulations, temporomandibular joints, sacroiliac joints, hip joints, knee joints and/or articulations of foot.

In some embodiments, an articular disease, disorder or condition may be caused by a protein deficiency or dysfunctions in a joint or a structure of a joint. In some embodiments, an articular disease, disorder or condition may be caused by a protein surplus, over expression, and/or over activation in a joint or a structure of a joint.

Exemplary articular diseases, disorders or conditions include, but are not limited to, rheumatoid arthritis, psoriatic arthritis, gout, pseudogout, tendinitis, bursitis, Carpal Tunnel Syndrome, osteoarthritis, synovitis, spondylitis, amyloidosis, lumbar spinal stenosis, and/or sacroiliac joint dysfunction.

mRNAs for Treating Articular Diseases, Disorders or Conditions

The present invention may be used to deliver any mRNAs that are suitable for treating articular diseases, disorders or conditions. In various embodiments, the present invention may be used to deliver an mRNA encoding a protein that is deficient in any of the articular diseases, disorders or conditions described herein. In such embodiments, the delivery of mRNA typically results in increased protein expression and/or activity in a joint sufficient to treat protein deficiency. In some embodiments, an mRNA suitable for the invention may encode a wild-type or naturally occurring protein sequence that normally present in a healthy joint. In some embodiments, an mRNA suitable for the invention may be a wild-type or naturally occurring sequence. In some embodiments, the mRNA suitable for the invention may be a codon-optimized sequence. In some embodiments, an mRNA suitable for the invention may encode an amino acid sequence having substantial homology or identity to the wild-type or naturally-occurring amino acid protein sequence (e.g., having at least 50%, 55%, 60%, 65%, 70%, 75%, 80%, 85%, 90%, 95%, 98% sequence identity to the wild-type or naturally-occurring sequence) that normally present in a healthy joint.

In some embodiments, the present invention may be used to deliver an mRNA encoding a therapeutic agent that inhibits, down-regulates, reduces a protein expression and/or activity, the excess level of which is associated with an articular disease, disorder or condition. Such a therapeutic agent may be a peptide, an antibody or other polypeptides or proteins.

In some embodiments, the present invention may be used to deliver mRNAs encoding an antibody, a soluble receptor or other binding proteins. Typically, suitable mRNAs encode an antibody that inhibits, down-regulates, or reduces a protein that is present in excess in amount and/or activity in an articular disease, disorder or condition. In some embodiments, suitable mRNAs encode an antibody that activates, up-regulates or increases a protein activity that is deficient in an articular disease, disorder or condition. Suitable exemplary antibodies encoded by mRNAs according to the present invention include, but are not limited to, antibodies against TNFα, IL-6, IL-1β, sTNFR-I, sTNFR-II, IL-2, IFN-γ, IL-18, IL-12, IL-12p40.

In some embodiments, the present invention may be used to deliver multiple distinct mRNAs, each distinct mRNA encoding at least one polypeptide. For example, each distinct mRNA may encode a heavy chain, a light chain of an antibody, or a fragment thereof (e.g., a variable region, an Fc region, etc.).

As used herein, the term "antibody" encompasses both intact antibody and antibody fragment. Typically, an intact "antibody" is an immunoglobulin that binds specifically to a particular antigen. An antibody may be a member of any immunoglobulin class, including any of the human classes: IgG, IgM, IgE, IgA, and IgD. Typically, an intact antibody is a tetramer. Each tetramer is composed of two identical pairs of polypeptide chains, each pair having one "light" (approximately 25 kD) and one "heavy" chain (approximately 50-70 kD). The N-terminus of each chain defines a variable region of about 100 to 110 or more amino acids primarily responsible for antigen recognition. The terms "variable light chain" (VL) and "variable heavy chain" (VH) refer to these corresponding regions on the light and heavy chain respectively. Each variable region can be further subdivided into hypervariable (HV) and framework (FR) regions. The hypervariable regions comprise three areas of hypervariability sequence called complementarity determining regions (CDR 1, CDR 2 and CDR 3), separated by four framework regions (FR1, FR2, FR2, and FR4) which form a beta-sheet structure and serve as a scaffold to hold the HV regions in position. The C-terminus of each heavy and light chain defines a constant region consisting of one domain for the light chain (CL) and three for the heavy chain (CH1, CH2 and CH3). A light chain of immunoglobulins can be further differentiated into the isotypes kappa and lamda.

In some embodiments, the terms "intact antibody" or "fully assembled antibody" are used in reference to an antibody that contains two heavy chains and two light chains, optionally associated by disulfide bonds as occurs with naturally-produced antibodies. In some embodiments, an antibody according to the present invention is an antibody fragment.

In some embodiments, the present invention can be used to deliver an "antibody fragment." As used herein, an "antibody fragment" includes a portion of an intact antibody, such as, for example, the antigen-binding or variable region of an antibody. Examples of antibody fragments include Fab, Fab', F(ab')$_2$, and Fv fragments; triabodies; tetrabodies; linear antibodies; single-chain antibody molecules; and multi specific antibodies formed from antibody fragments. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. In many embodiments, an antibody fragment contains a sufficient sequence of the parent antibody of which it is a fragment that it binds to the same antigen as does the parent antibody; in some embodiments, a fragment binds to the antigen with a comparable affinity to that of the parent antibody and/or competes with the parent antibody for binding to the antigen. Examples of antigen binding fragments of an antibody include, but are not limited to, Fab fragment, Fab' fragment, F(ab')$_2$ fragment, scFv fragment, Fv fragment, dsFv diabody, dAb fragment, Fd' fragment, Fd fragment, and an isolated complementarity determining region (CDR). Suitable antibodies include monoclonal antibodies, polyclonal antibodies, antibody mixtures or cocktails, human or humanized antibodies, chimeric antibodies, or bi-specific antibodies.

mRNA Synthesis mRNAs suitable for the present invention may be synthesized according to any of a variety of known methods. For example, mRNAs suitable for the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Desired mRNA sequence(s) according to the invention may be determined and incorporated into a DNA template using standard methods. For example, starting from a desired amino acid sequence (e.g., an enzyme sequence), a virtual reverse translation is carried out based on the degenerated genetic code. Optimization algorithms may then be used for selection of suitable codons. Typically, the G/C content can be optimized to achieve the highest possible G/C content on one hand, taking into the best possible account the frequency of the tRNAs according to codon usage on the other hand. The optimized RNA sequence can be established and displayed, for example, with the aid of an appropriate display device and compared with the original (wild-type) sequence. A secondary structure can also be analyzed to calculate stabilizing and destabilizing properties or, respectively, regions of the RNA.

Modified mRNA

In some embodiments, mRNA according to the present invention may be synthesized as unmodified or modified mRNA. Typically, mRNAs are modified to enhance stability. Modifications of mRNA can include, for example, modifications of the nucleotides of the RNA. An modified mRNA according to the invention can thus include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thiouracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thiouracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, mRNAs may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, mRNAs may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, O6-methylguanosine 5'-triphosphate, pseudouridine 5'-triphosphate, puromycin 5'-triphosphate or xanthosine 5'-triphosphate.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Cap Structure

In some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

Naturally occurring cap structures comprise a 7-methyl guanosine that is linked via a triphosphate bridge to the 5'-end of the first transcribed nucleotide, resulting in a dinucleotide cap of $m^7G(5')ppp(5')N$, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is $m^7G(5')ppp(5')G$, which has been used as the dinucleotide cap in transcription with T7 or SP6 RNA polymerase in vitro to obtain RNAs having a cap structure in their 5'-termini. The prevailing method for the in vitro synthesis of capped mRNA employs a pre-formed dinucleotide of the form $m^7G(5')ppp(5')G$ ("$m^7GpppG$") as an initiator of transcription.

To date, a usual form of a synthetic dinucleotide cap used in in vitro translation experiments is the Anti-Reverse Cap Analog ("ARCA") or modified ARCA, which is generally a modified cap analog in which the 2' or 3' OH group is replaced with —$OCH_3$.

Additional cap analogs include, but are not limited to, a chemical structures selected from the group consisting of $m^7GppppG$, $m^7GppppA$, $m^7GppppC$; unmethylated cap analogs (e.g., GpppG); dimethylated cap analog (e.g., $m^{2,7}GpppG$), trimethylated cap analog (e.g., $m^{2,2,7}GpppG$), dimethylated symmetrical cap analogs (e.g., $m^7Gppm^7G$), or anti reverse cap analogs (e.g., ARCA; $m^{7,2'Ome}GpppG$, $m^{72'd}GpppG$, $m^{7,3'Ome}GpppG$, $m^{7,3'd}GpppG$ and their tetraphosphate derivatives) (see, e.g., Jemielity, J. et al., "Novel 'anti-reverse' cap analogs with superior translational properties", RNA, 9: 1108-1122 (2003)).

In some embodiments, a suitable cap is a 7-methyl guanylate ("$m^7G$") linked via a triphosphate bridge to the 5'-end of the first transcribed nucleotide, resulting in $m^7G(5')ppp(5')N$, where N is any nucleoside. A preferred embodiment of a $m^7G$ cap utilized in embodiments of the invention is $m^7G(5')ppp(5')G$.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of $m^7G$ cap analogs are known in the art, many of which are commercially available. These include the $m^7GpppG$ described above, as well as the ARCA 3'-$OCH_3$ and 2'-$OCH_3$ cap analogs (Jemielity, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-1487 (2004)), phosphorothioate cap analogs (described in Grudzien-Nogalska, E., et al., RNA, 13: 1745-1755 (2007)), and cap analogs (including biotinylated cap analogs) described in U.S. Pat. Nos. 8,093,367 and 8,304,529, incorporated by reference herein.

Tail Structure

Typically, the presence of a "tail" serves to protect the mRNA from exonuclease degradation. The poly A tail is thought to stabilize natural messengers and synthetic sense RNA. Therefore, in certain embodiments a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, mRNAs include a 3' poly(A) tail structure. Typically, the length of the poly A tail can be at least about 10, 50, 100, 200, 300, 400 at least 500 nucleotides. In some embodiments, a poly-A tail on the 3' terminus of mRNA typically includes about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, a poly(U) tail may be used to instead of a poly(A) tail described herein. In some embodiments, a poly(U) tail may be added to a poly(A) tail described herein. In some embodiments, mRNAs include a 3' poly(C) tail structure. A suitable poly(C) tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly(C) tail may be added to a poly(A) and/or poly(U) tail or may substitute the poly(A) and/or poly(U) tail.

In some embodiments, the length of the poly(A), poly(U) or poly(C) tail is adjusted to control the stability of a modified sense mRNA molecule of the invention and, thus, the transcription of protein. For example, since the length of a tail structure can influence the half-life of a sense mRNA molecule, the length of the tail can be adjusted to modify the level of resistance of the mRNA to nucleases and thereby control the time course of polynucleotide expression and/or polypeptide production in a target cell.

5' and 3' Untranslated Region

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

Delivery Vehicles

According to the present invention, mRNA described herein may be delivered as naked RNA (unpackaged) or via delivery vehicles. As used herein, the terms "delivery vehicle," "transfer vehicle," "nanoparticle" or grammatical equivalent, are used interchangeably.

In some embodiments, mRNAs may be delivered via a single delivery vehicle. In some embodiments, mRNAs may be delivered via one or more delivery vehicles each of a different composition. According to various embodiments, suitable delivery vehicles include, but are not limited to polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates).

Liposomal Delivery Vehicles

In some embodiments, a suitable delivery vehicle is a liposomal delivery vehicle, e.g., a lipid nanoparticle. As used herein, liposomal delivery vehicles, e.g., lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphophilic polymers and surfactants (e.g., polymerosomes, niosomes, etc.). In the context of the present invention, a liposomal delivery vehicle typically serves to transport a desired mRNA to a target cell or tissue. The process of incorporation of a desired mRNA into a liposome is often referred to as "loading". Exemplary methods are described in Lasic, et al., FEBS Lett., 312: 255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating a mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Cationic Lipids

In some embodiments, liposomes may comprise one or more cationic lipids. As used herein, the phrase "cationic lipid" refers to any of a number of lipid species that have a net positive charge at a selected pH, such as physiological pH. Several cationic lipids have been described in the literature, many of which are commercially available. Particularly suitable cationic lipids for use in the compositions and methods of the invention include those described in international patent publications WO 2010/053572 (and particularly, CI 2-200 described at paragraph [00225]) and WO 2012/170930, both of which are incorporated herein by reference. In certain embodiments, the compositions and methods of the invention employ a lipid nanoparticles comprising an ionizable cationic lipid described in U.S. provisional patent application 61/617,468, filed Mar. 29, 2012 (incorporated herein by reference), such as, e.g., (15Z, 18Z)—N,N-dimethyl-6-(9Z,12Z)-octadeca-9,12-dien-1-yl) tetracosa-15,18-dien-1-amine (HGT5000), (15Z,18Z)—N,N-dimethyl-6-((9Z,12Z)-octadeca-9,12-dien-1-yl)tetracosa-4,15,18-trien-1-amine (HGT5001), and (15Z,18Z)—N,N-dimethyl-6-((9Z,12Z)-octadeca-9,12-dien-1-yl)tetracosa-5,15,18-trien-1-amine (HGT5002).

In some embodiments, provided liposomes include a cationic lipid described in WO 2013063468 and in U.S. provisional application entitled "Lipid Formulations for Delivery of Messenger RNA" filed concurrently with the present application on even date, both of which are incorporated by reference herein. In some embodiments, a cationic lipid comprises a compound of formula I-c1-a:

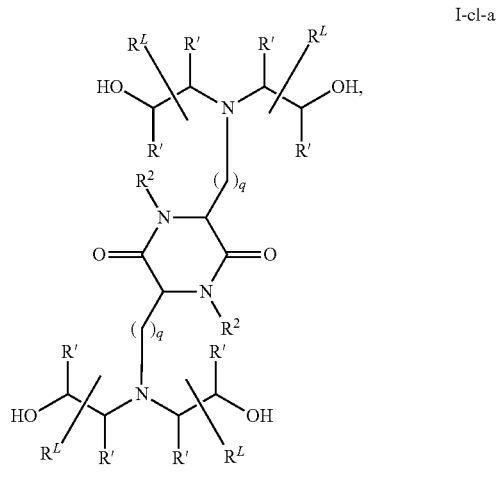

I-c1-a or a pharmaceutically acceptable salt thereof, wherein:
each $R^2$ independently is hydrogen or $C_{1-3}$ alkyl;
each q it is 2 to 6;
each R independently is hydrogen or $C_{1-3}$ alkyl;
and each $R^L$ independently is $C_{8-12}$ alkyl.

In some embodiments, each $R^2$ independently is hydrogen, methyl or ethyl. In some embodiments, each $R^2$ independently is hydrogen or methyl. In some embodiments, each $R^2$ is hydrogen.

In some embodiments, each q independently is 3 to 6. In some embodiments, each q independently is 3 to 5. In some embodiments, each q is 4.

In some embodiments, each R' independently is hydrogen, methyl or ethyl. In some embodiments, each R' independently is hydrogen or methyl. In some embodiments, each R' independently is hydrogen.

In some embodiments, each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ independently is n-$C_{10}$ alkyl.

In some embodiments, each $R^2$ independently is hydrogen or methyl; each q independently is 3 to 5; each R' independently is hydrogen or methyl; and each $R^L$ independently is $C_{8-12}$ alkyl.

In some embodiments, each $R^2$ is hydrogen; each q independently is 3 to 5; each R' is hydrogen; and each $R^L$ independently is $C_{8-12}$ alkyl.

In some embodiments, each $R^2$ is hydrogen; each q is 4; each R' is hydrogen; and each $R^L$ independently is $C_{8-12}$ alkyl.

In some embodiments, a cationic lipid comprises a compound of formula I-g:

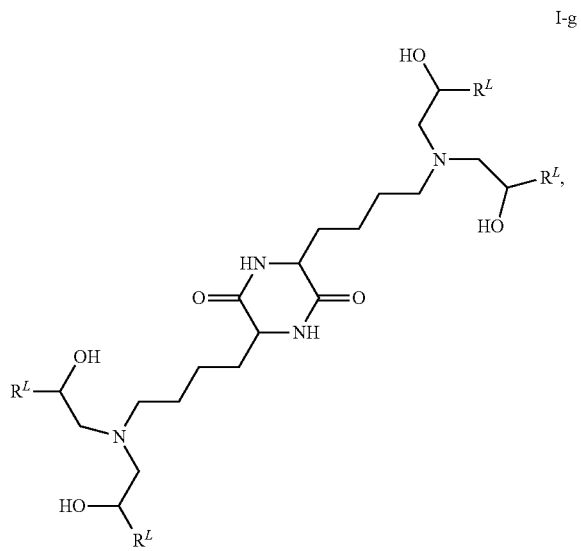

I-g or a pharmaceutically acceptable salt thereof, wherein each $R^L$ independently is $C_{8-12}$ alkyl. In some embodiments, each independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ is n-$C_{10}$ alkyl.

In particular embodiments, provided liposomes include a cationic lipid cKK-E12, or (3,6-bis(4-(bis(2-hydroxydodecyl)amino)butyl)piperazine-2,5-dione. Structure of cKK-E12 is shown below:

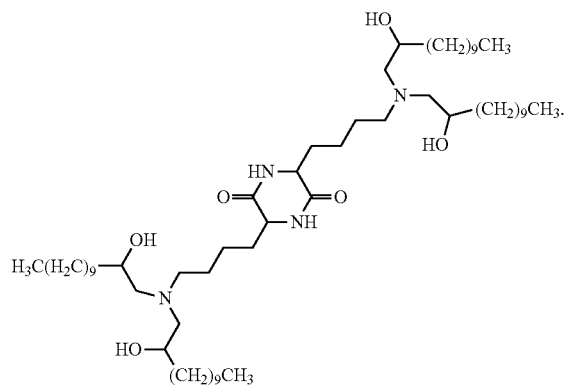

As described in the Examples section below, the present inventors observed that liposomes based on this particular class of cationic lipids, such as, those having a structure of formula I-c1-a or formula I-g described herein (e.g., cKK-E12) are unexpectedly effective in delivering mRNA and producing encoded protein in vivo. Although mRNA encoding PAH protein is used as an example in this application, it is contemplated that this class of cationic lipids having a structure of formula I-c1-a or formula I-g described herein (e.g., CKK-E12) can be useful in delivering any mRNA for highly efficient and sustained production of protein (e.g., therapeutic protein) in vivo. For example, cationic lipids having a structure of formula I-c1-a or formula I-g described herein (e.g., cKK-E12) can be used to deliver an mRNA that encodes one or more naturally occurring peptides or one or more modified or non-natural peptides. In some embodiments, cationic lipids having a structure of formula I-c1-a or formula I-g described herein (e.g., cKK-E12) can be used to deliver an mRNA that encodes an intracellular protein including, but not limited to, a cytosolic protein (e.g., a chaperone protein, an intracellular enzyme (e.g., mRNA encoding an enzyme associated with urea cycle or lysosomal storage disorders)), a protein associated with the actin cytoskeleton, a protein associated with the plasma membrane, a perinuclear protein, a nuclear protein (e.g., a transcription factor), and any other protein involved in cellular metabolism, DNA repair, transcription and/or translation). In some embodiments, cationic lipids having a structure of formula or formula i-g described herein (e.g., cKK-E12) can be used to deliver an mRNA that encodes a transmembrane protein, such as, an ion channel protein. In some embodiments, cationic lipids having a structure of formula I-c1-a or formula I-g described herein (e.g., cKK-E12) can be used to deliver an mRNA that encodes an extracellular protein including, but not limited to, a protein associated with the extracellular matrix, a secreted protein (e.g., hormones and/or neurotransmitters).

In some embodiments, one or more cationic lipids suitable for the present invention may be N-[1-(2,3-dioleyloxy) propyl]-N,N,N-trimethylammonium chloride or "DOTMA". (Feigner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido)ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP".

Additional exemplary cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylammonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethy 1-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP",1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl[1,3]-dioxolane or "DLin- -DMA", 2,2-dilinoleyl-4-dimethylaminoethyl[1,3]-dioxolane or "DLin-K-XTC2-DMA", and 2-(2,2-di((9Z,12Z)-octadeca-9,12-dien-1-yl)-1,3-dioxolan-4-yl)-N,N-dimethylethanamine (DLin-KC2-DMA)) (see, WO 2010/042877; Semple et al., Nature Biotech. 28: 172-176 (2010)), or mixtures thereof (Heyes, J., et al., J Controlled Release 107: 276-287 (2005); Morrissey, D V., et al., Nat. Biotechnol. 23(8): 1003-1007 (2005); PCT Publication WO2005/121348A1). In some embodiments, one or more of the cationic lipids comprise at least one of an imidazole, dialkylamino, or guanidinium moiety.

In some embodiments, the one or more cationic lipids may be chosen from XTC (2,2-Dilinoley1-4-dimethylaminoethyl-[1,3]-dioxolane), MC3 (((6Z,9Z,28Z,31Z)-heptatriaconta-6,9,28,31-tetraen-19-yl 4-(dimethylamino)butanoate), ALNY-100 ((3aR,5s,6aS)-N,N-dimethyl-2,2-di((9Z,12Z)-octadeca-9,12-dienyl)tetrahydro-3aH-cyclopenta[d][1,3]dioxol-5-amine)), NC98-5 (4,7,13-tris(3-oxo-3-(undecylamino)propyl)-N1,N16-diundecyl-4,7,10,13-tetraazahexadecane-1,16-diamide), DODAP (1,2-dioleyl-3-dimethylammonium propane), HGT4003 (WO 2012/170889, the teachings of which are incorporated herein by reference in their entirety), ICE (WO 2011/068810, the teachings of which are incorporated herein by reference in their entirety), HGT5000 (U.S. Provisional Patent Application No. 61/617,468, the teachings of which are incorporated herein by reference in their entirety) or HGT5001 (cis or trans) (Provisional Patent Application No. 61/617,468), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869).

In some embodiments, the percentage of cationic lipid in a liposome may be greater than 10%, greater than 20%, greater than 30%, greater than 40%, greater than 50%, greater than 60%, or greater than 70%. In some embodiments, cationic lipid(s) constitute(s) about 30-50% (e.g., about 30-45%, about 30-40%, about 35-50%, about 35-45%, or about 35-40%) of the liposome by weight. In some embodiments, the cationic lipid (e.g., cKK-E12) constitutes about 30%, about 35%, about 40%, about 45%, or about 50% of the liposome by molar ratio.

Non-Cationic/Helper Lipids

In some embodiments, provided liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other excipients, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

In some embodiments, provided liposomes comprise one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, The percentage of cholesterol-based lipid in the lipid nanoparticle may be greater than 5, %, 10%, greater than 20%, greater than 30%, or greater than 40%.

PEGylated Lipids

In some embodiments, provided liposomes comprise one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention in combination with one or more of the cationic and, in some embodiments, other lipids together which comprise the liposome. Contemplated PEG-modified lipids include, but are not limited to, a polyethylene glycol chain of up to 5 kDa in length covalently attached to a lipid with alkyl chain(s) of $C_6$-$C_{20}$ length. In some embodiments, a PEG-modified or PEGylated lipid is PEGylated cholesterol or PEG-2K. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613).

In some embodiments, particularly useful exchangeable lipids are PEG-ceramides having shorter acyl chains (e.g., $C_{14}$ or $C_{18}$). The PEG-modified phospholipid and derivatized lipids of the present invention may comprise a molar ratio from about 0% to about 15%, about 0.5% to about 15%, about 1% to about 15%, about 4% to about 10%, or about 2% of the total lipid present in the liposome.

Polymers

In some embodiments, a suitable delivery vehicle is formulated using a polymer as a carrier, alone or in combination with other carriers including various lipids described herein. Thus, in some embodiments, liposomal delivery vehicles, as used herein, also encompass polymer containing nanoparticles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDA, e.g., 25 kDa branched PEI (Sigma #408727).

According to various embodiments, the selection of cationic lipids, non-cationic lipids, PEG-modified lipids and/or polymers which comprise the lipid nanoparticle, as well as the relative molar ratio of such lipids to each other, is based upon the characteristics of the selected lipid(s)/polymers, the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus the molar ratios may be adjusted accordingly.

In some embodiments, the cationic lipids, non-cationic lipids, cholesterol, and/or PEG-modified lipids can be combined at various relative molar ratios. For example, the ratio of cationic lipid (e.g., cKK-E12, C12-200, HGT5001, etc.) to non-cationic lipid (e.g., DOPE, etc.) to cholesterol-based lipid (e.g., cholesterol) to PEGylated lipid (e.g., DMG-PEG2K) may be between about 30-60:20-35:20-30:1-15, respectively. In some embodiments, the liposome comprises cKK-E12, DOPE, cholesterol, and DMG-PEG2K. In some embodiments, the liposome comprises cKK-E12, DOPE, cholesterol, and DMG-PEG2K at a ratio of 50:25:20:5, 50:20:25:5, 50:27:20:3, 40:30:20:10, 40:30:25:5, or 40:32:25:3. In some embodiments, the liposome comprises C12-200, DOPE, cholesterol, and DMG-PEG2K. In some embodiments, the liposome comprises C12-200, DOPE, cholesterol, and DMG-PEG2K at a ratio of 50:25:20:5, 50:20:25:5, 50:27:20:3, 40:30:20:10, 40:30:25:5, or 40:32:25:3. In some embodiments, the liposome comprises HGT5001, DOPE, cholesterol, and DMG-PEG2K. In some embodiments, the lipsome comprises C12-200, DOPE, cholesterol, and DMG-PEG2K at a ratio 50:25:20:5, 50:20:25:5, 50:27:20:3, 40:30:20:10, 40:30:25:5, or 40:32:25:3.

Formation of Liposomes

The liposomal transfer vehicles for use in the present invention can be prepared by various techniques which are presently known in the art. The liposomes for use in provided compositions can be prepared by various techniques which are presently known in the art. For example, multi-lamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MLVs. Uni-lamellar vesicles (ULV) can then be formed by homogenization, sonication or extrusion of the multi-lamellar vesicles. In addition, unilamellar vesicles can be formed by detergent removal techniques.

In certain embodiments, provided compositions comprise a liposome wherein the mRNA is associated on both the surface of the liposome and encapsulated within the same liposome. For example, during preparation of the compositions of the present invention, cationic liposomes may associate with the mRNA through electrostatic interactions.

In some embodiments, the compositions and methods of the invention comprise mRNA encapsulated in a liposome. In some embodiments, the one or more mRNA species may be encapsulated in the same liposome. In some embodiments, the one or more mRNA species may be encapsulated in different liposomes. In some embodiments, the mRNA is encapsulated in one or more liposomes, which differ in their lipid composition, molar ratio of lipid components, size, charge (Zeta potential), targeting ligands and/or combinations thereof. In some embodiments, the one or more liposome may have a different composition of cationic lipids, neutral lipid, PEG-modified lipid and/or combinations thereof. In some embodiments the one or more lipisomes may have a different molar ratio of cationic lipid, neutral lipid, cholesterol and PEG-modified lipid used to create the liposome.

The process of incorporation of a desired mRNA into a liposome is often referred to as "loading". Exemplary methods are described in Lasic, et al., FEBS Lett., 312: 255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating a mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Nanoparticle Size

Suitable liposomes or other nanoparticles in accordance with the present invention may be made in various sizes. As used herein, the term "size", when used in connection with a nanoparticle, means the largest diameter of a nanoparticle. In some embodiments, a suitable nanoparticle has a size of or less than about 100 nm (e.g., of or less than about 90 nm, 80 nm, 70 nm, 60 nm, 50 nm, 40 nm, 30 nm, or 20 nm). In some embodiments, the nanoparticle has a size of or less than about 60 nm (e.g., of or less than about 55 nm, of or less than about 50 nm, of or less than about 45 nm, of or less than about 40 nm, of or less than about 35 nm, of or less than about 30 nm, or of or less than about 25 nm). In some embodiments, a suitable nanoparticle has a size ranging from about 10-100 nm (e.g., ranging from about 10-90 nm, 10-80 nm, 10-70 nm, 10-60 nm, 10-50 nm, 10-40 nm, or 10-30 nm).

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

Pharmaceutical Compositions and Administration

To facilitate expression of mRNA in vivo, delivery vehicles such as liposomes can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

In particular, provided mRNA (naked or nanoparticle-encapsulated or associated), and compositions containing the same, may be administered into a joint of a subject via intra-articular administration. As used herein, the terms "intra-articular injection", "intra-articular administration", "intra-articular delivery" or grammatical equivalents, refer to a procedure that causes direct or local administration into a joint. For example, provided mRNA (naked or nanoparticle-encapsulated or associated), and compositions containing the same, may be injected into the joint space for the purpose of relieving joint pain or inflammation.

Typically, provided mRNA (naked or nanoparticle-encapsulated or associated), and compositions containing the same, is administered at an effective amount or dose. As used herein, the "effective amount" refers to an amount, when administered once or according to a dosing regimen, is effective to achieve at least some stabilization, improvement or elimination of symptoms and other indicators as are selected as appropriate measures of disease progress, regression or improvement by those of skill in the art. In some embodiments, a suitable amount and dosing regimen is one that results in protein (e.g., antibody) expression or activity in the joint. In some embodiments, the expression and/or activity of the protein is detected in cartilage, ligament, muscle, synovial intimal cells, chondrocytes and/or fluids of the joint. In some embodiments, the expression and/or activity of the protein is detectable at least about 6 hours, 12 hours, 18 hours, 24 hours, 2 days, 3 days, 4 days, 5 days, 6 days, 1 week, 2 weeks, 3 weeks, 4 weeks, 1 month, or longer after a single administration.

Provided methods of the present invention contemplate single as well as multiple administrations of a therapeutically effective amount of mRNA or a composition described herein according to a dosing regimen. mRNA or a composition described herein can be administered at regular intervals, depending on the nature, severity and extent of the subject's condition. In some embodiments, a therapeutically effective amount of mRNA or a composition described herein may be administered periodically at regular intervals (e.g., once every year, once every six months, once every five months, once every four months, once every three months, bimonthly (once every two months), monthly (once every month), once every three weeks, biweekly (once every two weeks), weekly, once every three days, once every two days, daily or continuously). In some embodiments, mRNA or a composition described herein may be administered at variable intervals.

EXAMPLES

While certain compounds, compositions and methods of the present invention have been described with specificity in accordance with certain embodiments, the following examples serve only to illustrate the compounds of the invention and are not intended to limit the same.

Example 1

Exemplary Liposome Formulations for mRNA Delivery and Expression

This example provides exemplary liposome formulations for effective delivery and expression of mRNA in vivo.

Lipid Materials

The formulations described herein are based on a multi-component lipid mixture of varying ratios employing one or more cationic lipids, helper lipids and PEGylated lipids designed to encapsulate various nucleic acid-based materials. Cationic lipids can include (but not exclusively) DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869), cKK-E12 (3,6-bis(4-(bis(2-hydroxydodecyl)amino)butyl)piperazine-2,5-dione), HGT5000, HGT5001, HGT4003, ICE, dialkylamino-based, imidazole-based, guanidinium-based, etc. Helper lipids can include (but not exclusively) DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (2-dioleoyl-sn-glycero-3-phospho-(1'-rac-glycerol)), cholesterol, etc. The PEGylated lipids can include (but not exclusively) a poly(ethylene) glycol chain of up to 5 kDa in length covalently attached to a lipid with alkyl chain(s) of C6-C20 length. Polyethyleneimine can be linear or branched. For branched PEI, 25 kDa is preferred but not exclusive.

Messenger RNA Material

Codon-optimized firefly luciferase (FFL) messenger RNA was synthesized by in vitro transcription from a plasmid DNA template encoding the gene, which was followed by the addition of a 5' cap structure (Fechter, P.; Brownlee, G. G. "Recognition of mRNA cap structures by viral and cellular proteins" J. Gen. Virology 2005, 86, 1239-1249) and a 3' poly(A) tail of approximately 250 nucleotides in length as determined by gel electrophoresis. 5' and 3' untranslated regions present in each mRNA product are represented as X and Y, respectively and defined as stated (vide infra).

```
Codon-Optimized Firefly Luciferase (FFL) mRNA:
                                      [SEQ ID NO.: 1]
XAUGGAAGAUGCCAAAAACAUUAAGAAGGGCCCAGCGCCAUUCUACCCAC

UCGAAGACGGGACCGCCGGCGAGCAGCUGCACAAAGCCAUGAAGCGCUAC

GCCCUGGUGCCCGGCACCAUCGCCUUUACCGACGCACAUAUCGAGGUGGA

CAUUACCUACGCCGAGUACUUCGAGAUGAGCGUUCGGCUGGCAGAAGCUA

UGAAGCGCUAUGGGCUGAAUACAAACCAUCGGAUCGUGGUGUGCAGCGAG

AAUAGCUUGCAGUUCUUCAUGCCCGUGUUGGGUGCCCUGUUCAUCGGUGU

GGCUGUGGCCCCAGCUAACGACAUCUACAACGAGCGCGAGCUGCUGAACA
```

-continued

```
GCAUGGGCAUCAGCCAGCCCACCGUCGUAUUCGUGAGCAAGAAAGGGCUG

CAAAAGAUCCUCAACGUGCAAAAGAAGCUACCGAUCAUACAAAAGAUCAU

CAUCAUGGAUAGCAAGACCGACUACCAGGGCUUCCAAAGCAUGUACACCU

UCGUGACUUCCCAUUUGCCACCCGGCUUCAACGAGUACGACUUCGUGCCC

GAGAGCUUCGACCGGGACAAAACCAUCGCCCUGAUCAUGAACAGUAGUGG

CAGUACCGGAUUGCCCAAGGGCGUAGCCCUACCGCACCGCACCGCUUGUG

UCCGAUUCAGUCAUGCCCGCGACCCCAUCUUCGGCAACCAGAUCAUCCCC

GACACCGCUAUCCUCAGCGUGGUGCCAUUUCACCACGGCUUCGGCAUGUU

CACCACGCUGGGCUACUUGAUCUGCGGCUUUCGGGUCGUGCUCAUGUACC

GCUUCGAGGAGGAGCUAUUCUUGCGCAGCUUGCAAGACUAUAAGAUUCAA

UCUGCCCUGCUGGUGCCCACACUAUUUAGCUUCUUCGCUAAGAGCACUCU

CAUCGACAAGUACGACCUAAGCAACUUGCACGAGAUCGCCAGCGGCGGGG

CGCCGCUCAGCAAGGAGGUAGGUGAGGCCGUGGCCAAACGCUUCCACCUA

CCAGGCAUCCGCCAGGGCUACGGCCUGACAGAAACAACCAGCGCCAUUCU

GAUCACCCCGAAGGGGACGACAAGCCUGGCGCAGUAGGCAAGGUGGUGC

CCUUCUUCGAGGCUAAGGUGGUGGACUUGGACACCGGUAAGACACUGGGU

GUGAACCAGCGCGGCGAGCUGUGCGUCCGUGGCCCCAUGAUCAUGAGCGG

CUACGUUAACAACCCCGAGGCUACAAACGCUCUCAUCGACAAGGACGGCU

GGCUGCACAGCGGCGACAUCGCCUACUGGGACGAGGACGAGCACUUCUUC

AUCGUGGACCGGCUGAAGAGCCUGAUCAAAUACAAGGGCUACCAGGUAGC

CCCAGCCGAACUGGAGAGCAUCCUGCUGCAACACCCCAACAUCUUCGACG

CCGGGGUCGCCGGCCUGCCCGACGACGAUGCCGGCGAGCUGCCCGCCGCA

GUCGUCGUGCUGGAACACGGUAAAACCAUGACCGAGAAGGAGAUCGUGGA

CUAUGUGGCCAGCCAGGUUACAACCGCCAAGAAGCUGCGCGGUGGUGUUG

UGUUCGUGGACGAGGUGCCUAAAGGACUGACCGGCAAGUUGGACGCCCGC

AAGAUCCGCGAGAUUCUCAUUAAGGCCAAGAAGGGCGGCAAGAUCGCCGU

GUAAY
```

5' and 3' UTR Sequences
X (5' UTR Sequence) =

[SEQ ID NO.: 2]
```
GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACG
```

Y (3' UTR Sequence) =

[SEQ ID NO.: 3]
```
CGGGUGGCAUCCCUGUGACCCCUCCCCAGUGCCUCUCCUGGCCCUGGAAG

UUGCCACUCCAGUGCCCACCAGCCUUGUCCUAAUAAAAUUAAGUUGCAUC

AAGCU
```

OR (SEQ ID NO.: 4)
```
GGGUGGCAUCCCUGUGACCCCUCCCCAGUGCCUCUCCUGGCCCUGGAAGU

UGCCACUCCAGUGCCCACCAGCCUUGUCCUAAUAAAAUUAAGUUGCAUCA

AGCU
```

Exemplary Formulation Protocols

A. cKK-E12

Aliquots of 50 mg/mL ethanolic solutions of cKK-E12, DOPE, cholesterol and DMG-PEG2K were mixed and diluted with ethanol to 3 mL final volume. Separately, an aqueous buffered solution (10 mM citrate/150 mM NaCl, pH 4.5) of FFL mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=1.0 mg/mL FFL mRNA (encapsulated). $Z_{ave}$=78 nm; PDI: 0.13.

B. C12-200

Aliquots of 50 mg/mL ethanolic solutions of C12-200, DOPE, cholesterol and DMG-PEG2K were mixed and diluted with ethanol to 3 mL final volume. Separately, an aqueous buffered solution (10 mM citrate/150 mM NaCl, pH 4.5) of FFL mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.82 mg/mL FFL mRNA (encapsulated). $Z_{ave}$=83 nm; PDI: 0.13.

C. HGT5001

Aliquots of 50 mg/mL ethanolic solutions of HGT5001, DOPE, cholesterol and DMG-PEG2K were mixed and diluted with ethanol to 3 mL final volume. Separately, an aqueous buffered solution (10 mM citrate/150 mM NaCl, pH 4.5) of FFL mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=1.0 mg/mL FFL mRNA (encapsulated). $Z_{ave}$=80 nm; PDI: 0.13.

D. PEI 25 kDa branched PEI solution at a concentration of 1.34 mg/mL (pH 5.0) was mixed with equal volumes of FFL mRNA (1.0 mg/mL). The resultant formulation was stored at 2-8° C. Final concentration=0.50 mg/mL FFL mRNA.

Example 2

Efficient in Vivo Protein Production

This example demonstrates that administration of FFL mRNA results in successful protein production in vivo.

In Vivo Firefly Luciferase Protein Production Results

The production of firefly luciferase protein via codon-optimized FFL mRNA-loaded lipid and polymeric nanoparticles was tested in CD-1 mice as a single, bolus intra-articular injection. FIGS. 1A-4C represent the luminescence detected via in vivo bioluminescent imaging using an IVIS imager. Such luminescence was measured 24 hours post injection of FFL mRNA nanoparticles into wild type mice. Table 1 represents luminescence values after luciferin administration (total flux (photon/sec), 10 minutes post-luciferin). The mice were sacrificed twenty-four hours post-injection and organs were harvested (as described above).

TABLE 1

Quantitation of total luminescent flux (photons/sec) produced from active firefly luciferase protein derived from intra-articular administration of FFL mRNA-loaded nanoparticles. Values are reflective of protein produced 24 hours post-administration of test article. Total flux is measured 10 minutes after luciferin substrate administration.

| Carrier (Cationic Component) | mRNA | Dose (µg) | Total Flux (photon/sec) |
| --- | --- | --- | --- |
| cKK-E12 | FFL | 5.0 | 107,390,000 |
| C12-200 | FFL | 5.0 | 35,338,667 |
| HGT5001 | FFL | 5.0 | 10,915,000 |
| PEI (25 kDA branched) | FFL | 2.5 | 1,114,000 |

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of intra-articular delivery of messenger RNA (mRNA), comprising directly injecting into a joint of a subject in need thereof an effective amount of a composition comprising one or more mRNAs encoding an antibody, wherein the one or more mRNAs are encapsulated within one or more lipid nanoparticles comprising one or more cationic lipids, one or more non-cationic lipids, one or more cholesterol-based lipids and one or more PEG-modified lipids, such that the injecting of the composition results in expression of the antibody encoded by the one or more mRNAs in the joint for at least 6 hours.

2. The method of claim 1, wherein the composition is injected directly into the synovial cavity.

3. The method of claim 1, wherein the expression and/or activity of the one or more polypeptides is detected in cartilage, ligament, muscle, synovial intimal cells, chondrocytes and/or fluids of the joint.

4. The method of claim 1, wherein the expression and/or activity of the one or more polypeptides is detectable at least about 12 hours, 18 hours, 24 hours, 2 days, 3 days, 4 days, 5 days, 6 days, 1 week, 2 weeks, 3 weeks, 4 weeks, or 1 month post-injection.

5. The method of claim 1, wherein the one or more polypeptides encoded by the one or more mRNAs normally function in the joint.

6. The method of claim 1, wherein the one or more polypeptides encoded by the one or more mRNAs are anti-inflammatory.

7. A method of treating a joint disease, disorder or condition, comprising directly injecting into a joint one or more mRNAs using a method according to any one of the preceding claims, wherein directly injecting the composition into the joint treats the joint disease, disorder or condition.

8. The method of claim 7, wherein the joint disease, disorder or condition is an inflammatory disease, disorder or condition.

9. The method of claim 8, wherein the inflammatory disease, disorder or condition is arthritis.

10. The method of claim 7, wherein the composition is directly injected into the joint once a week.

11. The method of claim 7, wherein the composition is directly injected into the joint twice a month.

12. The method of claim 7, wherein the composition is directly injected into the joint once a month.

13. The method of claim 1, wherein the one or more cationic lipids comprise cKK-E12:

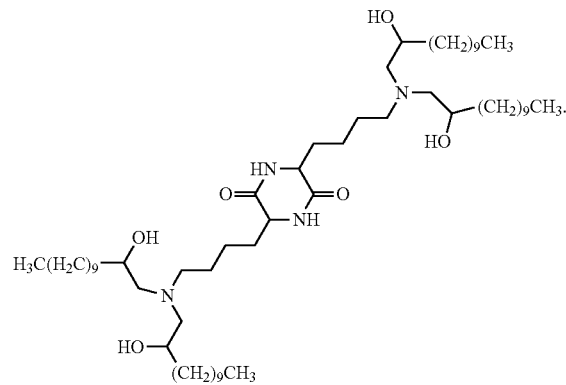

14. The method of claim 1, wherein the nanoparticles have a size less than about 40-100 nm.

15. The method of claim 1, wherein the one or more mRNAs comprise one or more modified nucleotides.

* * * * *